United States Patent [19]

Schroeder et al.

[11] 4,215,054

[45] Jul. 29, 1980

[54] PRODUCTION OF LIQUID ORTHO-PHTHALIC ACID AND ITS CONVERSION TO HIGH PURITY PHTHALIC ANHYDRIDE

[75] Inventors: Hobe Schroeder, Warrenville; George E. Kuhlmann, Naperville; Sydney G. Horsfield, Wheaton; David A. Palmer, Naperville, all of Ill.

[73] Assignee: Standard Oil Company (Indiana), Chicago, Ill.

[21] Appl. No.: 70,827

[22] Filed: Aug. 29, 1979

[51] Int. Cl.$^2$ ............................................ C07D 307/89
[52] U.S. Cl. ................................ 260/346.7; 260/346.4
[58] Field of Search ............................ 260/346.4, 346.7

[56] References Cited

U.S. PATENT DOCUMENTS

| | | | |
|---|---|---|---|
| 2,670,325 | 2/1954 | West et al. ................. | 260/346.7 X |
| 3,402,184 | 9/1968 | Berthoux et al. ................. | 260/346.4 |
| 3,484,458 | 12/1969 | Stein et al. ................. | 260/346.4 |
| 4,165,324 | 8/1979 | Schroeder et al. ................. | 260/346.7 |

*Primary Examiner*—Richard Raymond
*Attorney, Agent, or Firm*—Fred R. Ahlers; William T. McClain; William H. Magidson

[57] ABSTRACT

Phthalic anhydride of commercially acceptable quality can be recovered from the neat catalytic oxidation of liquid o-xylene with air in the presence of the catalysis system provided by cobalt, manganese and bromine conducted in a single step and in the presence of a small amount of benzoic acid to make miscible liquid o-phthalic acid and liquid oxylene conducted in a single step to an 80 to 90 mole percent yield of o-phthalic acid provided the resulting liquid oxidation effluent is subjected to rapid dehydration of o-phthalic acid to its anhydride and rapid evaporation of the anhydride, water and compounds boiling between water and said anhydride which evaporation entrains phthalide in the vapor mixture followed by contact of the vapor mixture with Pd/C and introducing the vapor mixture into a fractionating system whose reflux liquid is inert, boils at a temperature below the boiling temperature of phthalic anhydride and is a solvent therefor at a temperature below the freezing temperature of said anhydride whereby impure liquid anhydride is withdrawn as water-free liquid and charged to a step of heating with alkali metal hydroxide to remove phthalide and then fractionated to remove benzoic acid as a first fraction, high purity phthalic anhydride as a second fraction and materials boiling higher than the anhydride as a liquid third fraction.

4 Claims, No Drawings

PRODUCTION OF LIQUID ORTHO-PHTHALIC ACID AND ITS CONVERSION TO HIGH PURITY PHTHALIC ANHYDRIDE

TECHNICAL FIELD

This invention relates to the production of o-phthalic acid by the catalytic neat oxidation of liquid oxylene with air, the conversion of the resulting impure o-phthalic acid product to impure phthalic anhydride and its recovery as high purity phthalic anhydride product. More specifically the present invention comprises the cooperating combination of sequential steps of (a) such neat air oxidation of liquid o-xylene conducted in a single step in a continuous operation in the presence of a Co-Mn-Br system of catalysis and in the presence of from 5 to 25 weight percent acetic acid or benzoic acid as a miscibility agent to a liquid mixture comprising on a weight basis from 70 up to 85% o-phthalic acid, from 2 up to 21% water, from 0.3 up to 18% benzoic acid, from 0 up to 3.5% acetic acid, from 0.1 up to 3% o-toluic acid, from 0.1 up to 2% phthalide, from 0.2 up to 1.2% 2-carboxybenzaldehyde, and from 0.8 up to 2.2% higher boiling compounds including metal salts (from the catalyst metals) of organic acids, (b) the dehydration of said liquid mixture under conditions which rapidly evaporate phthalic anhydride (PAN) from the residue of such liquid, (c) removal of bromine from the vapor mixture by contacting it with a noble metal catalyst, (d) separation of the resulting mixture of vapors into a liquid water stream for discard and a liquid impure PAN by direct contact between said mixture of vapors and a reflux liquid, (e) removal of phthalide from said liquid impure PAN by heating it with an alkali metal hydroxide, and (f) separating materials boiling below and above PAN by fractionation to recover a PAN product fraction which as a liquid has an initial and aged color meeting the commercial specifications therefor.

RELATED PATENT APPLICATIONS

U.S. Patent Application Ser. No. 961,763 filed Nov. 17, 1978 describes the single step neat continuous oxidation of liquid o-xylene; Ser. No. 21,342 filed Mar. 19, 1979 discloses bromine removal from impure PAN vapors; Ser. No. 898,930 filed Feb. 1, 1979, now U.S. Pat. No. 4,105,324, discloses phthalide removal from impure PAN by the use of an alkali metal hydroxide; Ser. No. 969,879 filed Dec. 15, 1978 discloses the separation of water by contacting a mixture of water and PAN vapors with a reflux liquid; and Ser. No. 22,431, now abandoned, discloses the rapid dehydration of o-phthalic acid in and rapid evaporation of PAN from the liquid mixture containing 70 to 85 weight percent o-phthalic acid.

STATE OF THE ART

The present invention comprising the combination of cooperating steps of production of o-phthalic acid, its conversion to phthalic anhydride and the purification of said anhydride represents a novel, unique continuous process. Since phthalic anhydride (PAN) has long been produced by a route starting with the air oxidation of a vapor phase of naphthalene or o-xylene in the presence of a solid vanadium-containing catalyst, the art pertaining to the separation of PAN from spent air exiting such oxidation and the purification of such PAN has not been found to be pertinent to the present inventive combination of cooperating steps.

British patent specification No. 856,245, published Dec. 14, 1960 is directed to a two-step catalytic neat oxidation of liquid o-xylene as a method of producing PAN because attempts at conducting a single-step neat oxidation of o-xylene were not successful beyond about 70 mole percent conversion. The first step of such two-step process is a mild oxidation of liquid o-xylene in the presence of cobalt alone or in combination with a source of bromine. The incomplete oxidation products of the first step with little or no xylene present are oxidized in the second step under more vigorous conditions using a Co-Mn-Br system of catalysis. The second step produces an impure liquid phthalic anhydride product. Such impure liquid phthalic anhydride is refluxed with water for 90 minutes to precipitate o-phthalic acid which is recovered by filtration and the filter cake extracted with ether. The dried ether extracted filter cake is said to be 98% pure o-phthalic acid. However, the 2% impurities were not identified but probably did not contain catalyst metals. No processing scheme was presented for conversion of such 98% pure o-phthalic acid to phthalic anhydride of a commercially acceptable quality.

According to U.S. Pat. No. 3,402,184 o-xylene is oxidized with air in the presence of a liquid phase of an acetic acid solution containing cobalt, manganese and bromine ions as components of catalysis. The liquid effluent from such an oxidation contains phthalic anhydride dissolved in the acetic acid. According to the patent, the liquid effluent is diluted with water and the diluted effluent is heated to its boiling point temperature to hydrolyze the anhydride to o-phthalic acid which in part precipitates from the diluted acetic acid solution. The o-phthalic acid precipitate is recovered by means for effecting solid-liquid separation (e.g., filtration). While the separated o-phthalic acid precipitate was thermally converted back to phthalic anhydride, such anhydride had only a quality of partially purified anhydride and, as such, was not of commercially acceptable quality. Also a substantial proportion of the o-phthalic acid produced by hydrolysis of the anhydride dissolved in the liquid oxidation effluent remained dissolved in the dilute acetic acid solution. For the foregoing process to be commercially attractive such dissolved o-phthalic acid must be separated from the dilute acetic acid solution before or during recovery of acetic acid for its reuse in the o-xylene oxidation. Such second crop of o-phthalic acid or its anhydride derivative would be contaminated with catalyst metals.

With respect to the understanding and practice of the present inventive process, the fluid mixture containing mainly o-phthalic acid is produced according to the foregoing patent application Ser. No. 961,763, by the single-step, continuous neat oxidation of liquid o-xylene with air or air fortified with oxyen gas to an oxygen content of up to 50 volume percent, at a temperature in the range of from 200° C. up to 235° C. in the presence of a solution of cobalt, manganese, and bromine ions as components of catalysis in a solvent comprising o-phthalic acid as a major component, from 2 up to 21 weight percent water, also including from 5 up 20 weight percent, based on the xylene, of acetic acid or benzoic acid to make miscible an o-xylene phase and an ophthalic acid phase otherwise immiscible; and under a gauge pressure in the range of from 23 up to at least 31 kg/cm$^2$ to maintain not only a liquid phase of said solution but also to maintain equilibrium conditions favoring retention of o-phthalic acid in the free acid form rather than in the anhydride form. The components of catalysis are present in an amount based on one gram mole of oxylene charged of from 0.5 up to 10 milligram atoms of cobalt, of from 0.15 up to 20 milligram atoms of manganese, and from 0.225 up to less than 60 milligram atoms of bromine.

In general, in the continuous catalytic neat (no extraneous reaction medium solvent) air oxidation of liquid o-xylene, conducted by methods prior to that of Ser. No. 961,763, a phase miscibility problem begins to occur when the liquid reaction mixture contains about 40 weight percent o-phthalic acid. At such concentration of o-phthalic acid the o-xylene fed into the liquid reaction mixture becomes substantially insoluble therein or substantially immiscible therewith and forms a separate phase even within the stirred liquid reaction mixture. The catalyst components stay dissolved in the liquid o-phthalic acid in the reaction mixture and hence are not as effectively available for the oxidation of o-xylene. The oxidation continues but its vigor diminishes until the rate of oxidation becomes commercially unacceptable. Such vigor-diminishing condition is readily observable from the volume ratio of o-xylene to water condensed from the exhaust from the oxidation zone. Such volume ratio is normally in the range of from 0.3:1.0 to 0.5:1.0 but the reaction×s diminishing vigor is indicated by change of such ratio of 1:1 and finally to 2:1 for an unacceptable reaction rate.

However, by continuously adding either acetic acid or benzoic acid to the oxidation zone in an amount of from 5 up to 25, preferably 7 to 10, weight percent of the o-xylene, as is done in the one-step continuous oxidation of Ser. No. 961,763, such condition of formation of two distinct substantially immiscible phases does not occur and a commercially acceptable rate of conversion of o-xylene and yield of o-phthalic acid can be obtained by the one-step continuous process.

Such use of acetic acid or liquid benzoic acid can be made by the separate addition of said acid to the stirred reaction zone simultaneously with the addition of a source of molecular oxygen gas, oxylene and an aqueous solution of components of catalysis, or by using the acetic or liquid benzoic acid as solvent carrier of the components of catalysis and the requisite water, or in the case of using benzoic acid, to predissolve it in the o-xylene fed to the stirred oxidation zone. Not only does such use of acetic or benzoic acid avoid the formation of two immiscible liquid phases, but the use of said miscibility-assisting acid also makes the reaction more tolerant of higher water, above 7 weight percent and up to 21 weight percent water, in the reaction mixture.

While acetic acid and benzoic acid do suppress the total combustion of o-xylene, acetic acid suppresses such total combustion at the sacrifice of 50% of the acetic acid to its total combustion. The neat oxidation of o-xylene does produce some small amount of benzoic acid, less than 1.0 mole percent of the xylene. Since benzoic said suppresses total combustion of o-xylene without itself being more than slightly consumed by total combustion, and since benzoic acid must be removed from the reaction mixture, it is preferred to use benzoic acid as the miscibility aid according to the present invention. Acetic acid would also have to be removed from the PAN product but requires extra processing to do so to be able to recycle the acetic acid to the oxidation.

In Table I to follow, typical compositions are given for the final reaction effluents from the continuous one-step operation of the above characterized neat catalytic oxidations of liquid o-xylene with air. The components are shown in weight percent of the composition.

TABLE I

Reaction Effluent Compositions

| Components: | 1 | 2 |
|---|---|---|
| o-Phthalic Acid | 71.0 | 76.0 |
| o-Toluic Acid | 1.05 | 1.92 |
| Phthalide | 1.22 | 1.92 |
| 2-Carboxybenzaldehyde | 0.22 | 0.13 |
| High Boilers | 2.17 | 2.89 |
| Water | 20.50 | 5.75 |
| Benzoic Acid | 0.35 | 11.20 |
| Acetic Acid | 3.53 | 0 |

STATEMENT OF THE INVENTION

The present invention comprises the cooperating sequential continuous steps of (a) single-step neat oxidation of liquid oxylene with air or air fortified with oxygen gas up to 50 vol. % $O_2$, in a stirred tank-type oxidation zone, at a temperature of from 200° C. up to 235° C. and a gauge pressure of from 23 up to 31 kg/cm² in the presence of liquid o-phthalic acid, in the presence of 2 to 21 weight percent water, and based on 1.0 gram mole of oxylene in the presence of from 5 to 20 grams of benzoic acid, from 0.5 up to 10 milligram atoms of cobalt, from 0.15 up to 20 milligram atoms of manganese and from 0.225 up to about 60 milligram atoms of bromine whereby a liquid mixture containing 70 to 85 weight percent o-phthalic acid is formed; (b) rapid dehydration of o-phthalic acid to its anhydride and its evaporation from the liquid mixture; (c) removal of bromine from the vapor mixture by contacting it with a noble metal, preferably palladium or platinum disposed on the surface of activated carbon; (d) separation of water vapor from vapors of phthalic anhydride and compounds vaporized and entrained therewith during said dehydration-evaporation step by direct contact with a water-immiscible, heat-exchange liquid boiling at a temperature below the boiling temperature of phthalic anhydride and liquid at a temperature above the freezing point temperature of phthalic anhydride; (e) removal of phthalide from phthalic anhydride by heating a mixture thereof and phthalide to a temperature of at least 200° C. in the presence of a catalytic amount of alkali metal hydroxide having a molecular weight upward from 40; and (f) separation of commercial quality phthalic anhydride from said phthalide-free mixture by fractionating it at subatmospheric pressure in a known manner into a first fraction containing mainly benzoic acid, a phthalic anhydride product fraction and a bottoms fraction containing compounds boiling at a temperature above the boiling temperature of phthalic anhydride.

SPECIFIC EMBODIMENTS

A. Continuous One-Step Oxidation

The operating parameters of the single-step continuous process for the oxidation of liquid o-xylene to o-phthalic acid are an oxidation zone temperature in the range of 200° C. up to 235° C. and gauge pressure in the range of from 23 up to 31 kg/cm²; a water concentration of from 2 up to 21 weight percent in the liquid reaction mixture in the stirred oxidation zone; the use of 5 up to 20 grams of benzoic acid per gram mole of o-xylene; the use of air, air enriched with oxygen or molecular oxygen gas in an amount related to o-xylene charged so that the exhaust from the oxidation zone contains at least one volume percent oxygen; and the use of the components of catalysis per gram mole of o-xylene in the range of from 0.5 up to 10 milligram atoms of cobalt, of from 0.15 up to 20 milligram atoms of manganese, and from 0.225 to less than 60 milligram atoms of bromine.

A suitable residence time in the stirred oxidation zone under the foregoing conditions will be from 60 up to 80, preferably from 90 up to 120 minutes. By "residence time," as used in reference to the conduct of this continuous oxidation step, is meant the ratio of volume (actual, not aerated expanded volume) retained in the oxidation zone to the total volume rate (volume per minute) of liquids leaving said zone.

For the sake of convenience with respect to the use of benzoic acid as the preferred miscibility aid, the solubility of benzoic acid in 100 grams of o-xylene is: 7.5 grams of benzoic acid at 25° C., 10 grams of benzoic acid at 30° C., and 20 grams of benzoic acid at 52° C.

B. Dehydration of o-Phthalic Acid to PAN

The recovery of a partially purified phthalic anhydride (PAN) from the liquid effluent produced by the oxidation step and containing, on a weight basis, from 70% up to 85% o-phthalic acid, from 2 up to 21% water, from 0.2 up to 18% benzoic acid, from 0 up to 3.5% acetic acid, and impurity amounts of various oxygen-containing aromatic compounds boiling above and below the boiling temperature of PAN including precursors of o-phthalic acid as well as compounds containing cobalt, manganese and bromine derived from the catalysis used for the preparation of such effluent, is characterized by the continuous in situ rapid dehydration of o-phthalic acid to PAN and flash evaporation of it from the liquid effluent leaving a fluid residue containing the materials boiling above the boiling temperature of PAN, and continuously removing the vapor fraction and the liquid residue fraction as separate streams from the site of such dehydration and flash evaporation.

Such rapid dehydration to and evaporation of partially purified PAN can be suitably effected by introducing the fluid oxidation product into a combination dehydration-evaporation zone maintained at a pressure in the range of from 760 mm Hg (one atmosphere) down to 0.05 atmosphere, preferably in the range of from 0.3 down to 0.1 atmosphere, and at a temperature in the range of from 180° C. up to 250° C. and removing from such zone the separate vapor fraction stream and the liquid residue stream.

For efficient fluid flow out of the dehydration-evaporation zone, the fluid residue, i.e., a mixture containing materials boiling at a temperature above the boiling temperature of PAN, can contain from 10 up to 60 weight percent PAN as a viscosity-reducing flux. Loss of PAN to the residue will be from one up to four weight percent of the PAN equivalent of o-phthalic acid in the feed. Much of the residue's PAN can be extracted by water as o-phthalic acid.

The mixture of vapors withdrawn from the heating-vaporizing zone comprises water as the non-organic portion and the organic portion comprising mainly (81–99 wt. %) PAN together with benzoic acid (up to 13 wt. %) and/or acetic acid (up to 5 wt. %); the precursors (o-toluic acid, 2-carboxybenzaldehyde and phthalide) which amount in toto to from 1.13% up to 1.8% by weight; and the accompanying bromine-containing compounds in amounts of less than 1000 ppm.

Removing the fraction comprising the mixture of vapors and the fluid metals-containing bottoms fraction from the heating and vaporizing zone substantially as rapidly as such fractions are formed minimizes contact between liquid PAN and the metals-containing bottoms fraction. Such minimum contact is an essential critical feature of the present invention. We have found that moderate to relatively long contact between liquid PAN and said metals-containing residue fraction enhances decomposition of PAN thereby lowering its yield and adds, in some way, new colored or color-forming impurities which cannot be removed from PAN by any commercially feasible and economic process.

The liquid effluent from the single-step neat oxidation of liquid o-xylene is obtained therefrom at a temperature of from 200° C. up to 235° C. and a pressure of from 23 up to 31 kg/cm$^2$. Since step (b) is conducted at a lower pressure, i.e., from one atmosphere (760 mm Hg) down to 0.05 atmosphere (40 mm Hg), sudden decompression of said liquid effluent to such lower pressure could cause solidification of the effluent unless it is maintained at a temperature at which the effluent remains a liquid. This can be readily accomplished by combining the oxidation effluent with additional liquid water at the effluent's pressure to increase the water content to 15 to 20 weight percent of the diluted effluent and maintaining its temperature at 200° C. to 220° C. and then feeding such diluted effluent into the dehydration and evaporation zone. Alternatively, the liquid effluent can be used directly by combining it with a large volume of liquid residue (PAN and water depleted effluent rapidly circulating from the dehydration-evaporation zone through indirect heating and back to the dehydration-evaporation zone).

C. Removal of Bromine

The bromine content of partially purified phthalic anhydride obtained from step (a) can be diminished to less than 3 ppm by weight based on the anhydride by contacting the vapors of such partially purified anhydride and water vapor with a particulated solid catalyst comprising from 0.01 up to 10 weight percent, preferably 0.1 to 1.0 weight percent, metallic palladium or platinum disposed on the surface of carbon or charcoal (hereafter Pd/C or Pt/C). Such carbon or charcoal is known as activated carbon. Suitably such activated carbon has a surface area to mass ratio of at least 100 and up to 3000 m$^2$/g, preferably from 500 to 2000 m$^2$/g.

Such contact treatment is of short duration. Merely passing the vapors of the partially purified phthalic anhydride through a short bed of such particulated catalyst will provide a sufficient contact time for the practice and the purposes of this invention.

It is indeed surprising that merely contacting the vapors of the partially purified phthalic anhydride and small amount of water vapor with the Pd/C or Pt/C catalyst in the absence of hydrogen can effect the debromination to a concentration of less than 3 ppm by weight of the anhydride.

The limit of the x-ray fluorescence detection analytical technique to detect bromine in a composition containing phthalic anhydride is 3 weight part of bromine per $1.0 \times 10^6$ (million) weight parts of the anhydride, i.e., 0.0003 wt. %. Thus "less than 3 ppm by weight of bromine based on the anhydride" means no detectable bromine.

We have discovered that the treatment of liquid partially purified PAN with hydrogen and Pd/C catalyst does not effectively cause debromination of the bromoaromatic impurity: ArBr, as might be expected according to the equation

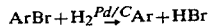

$$ArBr + H_2 \xrightarrow{Pd/C} Ar + HBr$$

However, when water vapor is present, effective debromination of the aromatic impurity (ArBr) possibly occurs in the vapor state in the presence of Pd/C catalyst according to the equation

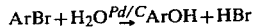

$$ArBr + H_2O \xrightarrow{Pd/C} ArOH + HBr$$

Thus, the presence of a "small amount" of water with partially purified PAN would be a quantity of water at least equal to 0.25 times the weight percent of bromine present. Greater quantities of water, for example, up to 20 weight percent of the mixture of PAN and water can be contacted with the Pd/C catalyst without diminishing the debromination effectiveness.

The amount of catalyst useful in step (b) of this invention depends on the Pd or Pt content of the catalyst. The Pd/C or Pt/C particulated catalyst will provide a low pressure drop bed when the catalyst particles are of a size not smaller than 1.69 mm nor larger than 4.75 mm. That is, such particles will not pass through a sieve with 1.68 mm openings but will pass through a sieve with 4.76 mm openings. The catalyst bed need not consist of a single particle size but can comprise a mixture of particle from 1.69 up to 4.75 mm. Such a bed of diverse particle sizes having a Pd or Pt content of from 0.01 up to 10 weight percent can be, with respect to the vapor mixture to pass therethrough, of from 10 to 1000 grams of catalyst per kilogram of the vapor mixture.

The temperature of the vapor mixture from step (a), that is from 180° up to 250° C., will provide an adequate catalyst bed temperature for the debromination according to this step (b) of the present invention.

D. Separation of PAN From Mixture of PAN and Water Vapors

The separation of phthalic anhydride from a vapor mixture containing 60 to 85 weight percent of said anhydride and 25 to 10 weight percent water vapor with the remainder comprising vapors of benzoic acid, o-toluic acid and materials boiling near or just above said anhydride withdrawn from the previous step involves contacting such vapor mixture in countercurrent flow with a reflux liquid at a temperature below the boiling point of phthalic anhydride to condense it and dissolve its condensate. Said separation is effected at a pressure of from 1.0 atmosphere down to 0.05 atmosphere, preferably from 0.3 to 0.13 atmosphere by exchange of heat from the vapor mixture to vaporize some of the reflux liquid. Its vapors and water vapor move upward in a rectification zone countercurrent to the flow of reflux liquid and form a vapor mixture enriched in water vapor and vapor of the reflux liquid but depleted in vapors of benzoic acid, toluic acid and aromatic compounds having boiling temperatures above that of water but below such acids. Such enrichment in water vapor and vapors of reflux liquid continues until the rising vapor mixture contains substantially only vapors of water and the reflux liquid. The mixture of substantially only vapors of water and reflux liquid is cooled to a temperature below the boiling temperature of water, thereby condensing both the reflux liquid and water. The water condensate separates from the reflux liquid's condensate. The water layer is discarded. The cool reflux liquid condensate layer is recycled to said rectification separation.

The reflux liquid moves from the rectification zone down through said contact with the feed vapor mixture to a stripping zone wherein the reflux liquid carrying phthalic anhydride condensate as dissolved liquid and/or solvent becomes enriched with respect thereto and with respect to benzoic and o-toluic acids and phthalide. The reflux liquid containing phthalic anhydride, benzoic acid, otoluic acid and phthalide is heated to a temperature which vaporizes the reflux liquid but not phthalic anhydride but rather the heating leaves the anhydride as a liquid in which phthalide, benzoic acid and o-toluic acid become dissolved.

Such a concept for PAN separation requires as the reflux liquid a substantially pure single compound or a mixture of boiling point-related compounds so that there is no component of the reflux liquid which will remain with and contaminate phthalic anhydride. The reflux liquid must be an inert solvent or absorbent for phthalic anhydride, benzoic acid, and o-toluic acid at low temperatures, e.g., below the anhydride's freezing point and up to its melting point, and miscible with said benzene carboxylic acids at higher temperatures between their melting and boiling point temperatures. The reflux liquid must be immiscible and unreactive with water to facilitate their separation for recycle of the reflux liquid and minimize its loss in the separated water condensate. The reflux liquid must have a vapor pressure higher than the vapor pressure of phthalic anhydride to be readily separable therefrom but sufficiently low to remain substantially liquid after contact with the hot, 180° to 235° C. feed, and move through the stripping zone. Lastly, the reflux liquid should not form an azeotrope with either one or all of phthalic anhydride, benzoic acid or o-toluic acid.

The most convenient use of such reflux liquid is in a combination of a rectification zone above a feed zone, a stripping zone below the feed zone, a zone for vaporizing the reflux liquid at a temperature above the melting point but below the boiling point temperatures of phthalic anhydride and transferring the reflux liquid vapors to contact the reflux liquid carrying in solution or by absorption phthalic anhydride, benzoic acid and o-toluic acid, and a zone to receive and cool the mixture of water and reflux liquid vapors to condense them for their separation and recycle of the reflux liquid condensate. Said combination of condensation zone, rectification zone, feed zone, stripping zone and reboiling zone define, of course, a fractionation system (e.g., a fractionating tower).

Methylbenzoate is the preferred reflux liquid to use in the fractionation system for effectively removing water vapor from a mixture thereof with vapors of phthalic anhydride, benzoic acid, otoluic acid and phthalide. Pseudocumene (1,2,4-trimethylbenzene) can also be used as such reflux liquid.

The amount of methylbenzoate reflux liquid used relative to the amount of water present in the feed can vary from 8:1 up to 20:1 on a liquid volume ratio basis. Typically from 0.7 up to 0.9 mole of methylbenzoate is refluxed per mole of vapor fed to the fractionation system. The amount of pseudocumene used can be varied from 1.5 up to 3.0 moles per mole of the vapor mixture fed to the fractionation system.

One example of such fractionation system is provided by a top recycle tray, a 15-tray column for rectification zone below the recycle tray, a feed tray below the rectification zone, and a 20-tray column as the stripping zone below the feed tray. Such trays have a 50% to 85% separation efficiency. Both of said columns are vacuum jacketed as are the feed and recycle trays. An externally heated reboiler having a side outlet for liquid removal supplies heat for the stripping zone by vaporizing at least the reflux liquid flowing down the stripping zone into said reboiler. The reboiler is operated at a temperature of from 200° C. up to 250° C. and a pressure of from 0.19 up to 0.33 atmosphere; i.e., from 150 mm Hg up to 250 mm Hg.

As it will be appreciated by a chemical process design engineer, such fractionation system towers or columns can be any of the trayed or packed columns generally useful for fractionation.

Vapor from above the recycle tray is transferred through a heat traced line to a condenser cooled to a temperature of from 25° up to 43° C. above a decanter from the side of which the top aqueous phase flows into a receiver and from the bottom of which the reflux liquid condensate returns through a reflux control valve and meter. A water cooled knockback condenser is in the vacuum line to minimize removal of low boiling compounds into the vacuum system. Pressure at the top of the rectification column can be maintained at 150 torr (0.2 atmosphere) by a control valve operated by a pneumatic controller and an absolute pressure transmitter.

E. Removal of Phthalide From PAN

The liquid mixture containing mainly phthalic anhydride (PAN) and impurity concentrations of benzoic acid, phthalide, o-toluic acid and 2-carboxybenzaldehyde, if any of the latter be present, is removed from the reboiler of the preceding step at a temperature of 200° C. up to 250° C. and is held at that temperature or even heated under pressure up to 350° C. in the presence of a catalytic amount, from 1.0 up to 10 milligram moles per one gram mole of impure phthalic anhydride, of an alkali metal hydroxide having a molecular weight of at least 40 (e.g., molecular weight of 40, 56, 102 or 150). No distillation or solid-liquid separation is used in this step of phthalide removal. Rather only the foregoing heating in the presence of said alkali metal hydroxide causes the phthalide per se to disappear (i.e., no longer analytically detectable) from the impure PAN.

The duration of such heating of impure PAN in the presence of said alkali metal hydroxide varies with the concentration of the anhydride used and with the temperature of such heating. At equal concentrations and heating temperatures, the relative activities of the hydroxodes are of the order of: $Na<K<Rb<Cs$. The phthalide removal activities of the different alkali metal hydroxides can be illustrated by their use at 275° C. for four hours at the concentration of 3.7 milligram moles per one gram mole of impure PAN containing 0.78 weight percent phthalide. After such treatment the samples of PAN were found by analysis to contain the residual concentrations of phthalide shown in TABLE II to follow.

TABLE II

| Hydroxide | Residual Phthalide, wt.% |
| --- | --- |
| LiOH | 0.37 |
| NaOH | 0.21 |
| KOH | 0.008 |
| RbOH | 0.007 |

TABLE II-continued

| Hydroxide | Residual Phthalide, wt.% |
| --- | --- |
| CsOH | <0.001* |
| L6 *Limit of detectability is 10 ppm (0.001%) by weight. | |

Based on activity for phthalide removal as indicated in Table II the preferred alkali metal hydroxides are those having a molecular weight of 56, 102 and 150; i.e., the hydroxides of potassium, rubidium and cesium. Based on economics the use of potassium hydroxide is preferred because on a unit weight basis the hydroxides of rubidium and cesium costs are several hundred times that of potassium hydroxide. Therefore the most preferred alkali metal hydroxide is potassium hydroxide.

The varience of activity with temperature of the alkali metal hydroxides in this step can be illustrated by the use of 3.7 milligram moles per one gram mole of impure PAN and determining the half period (time for phthalide concentration to diminish by one-half) at different temperatures. Such half periods for said concentration of KOH are 10 minutes at 275° C., 103 minutes at 250° C. and (by extrapolation) more than ten days at 200° C.

The normal (760 mm Hg) boiling temperature of the impure PAN is about 275° C. Thus, this step which on the basis of operating time can be carried on suitably at at a temperature from 250° C. up to 350° C. and preferably at a temperature of from 275° C. up to 300° C. Thus, the operating pressure is rather moderate and can be from one atmosphere (0 kg/gauge pressure) with added inert gas up to 1.45 atmosphere (0.5 kg/cm² gauge pressure) at 300° C. with no added inert gas.

Impure PAN having a phthalide content of up to 2.0 weight percent can upon treatment at 275° C. for four hours with 3.7 milligram moles KOH per one gram mole of impure PAN decrease in phthalide content to less than 0.001 weight percent.

F. PAN Recovery by Fractionation

Following the foregoing step of phthalide removal the hot impure PAN is charged directly to a fractionation step conducted in known manner. Such fractionation of impure PAN containing benzoic acid, o-toluic acid and 2-carboxybenzaldehyde can be conducted at an operating pressure in the range of from 20 mm Hg up to 760 mm Hg absolute (i.e., from 0.026 up to 1.0 atmospheres). For continuous operation the fractionation is conducted in two towers. The benzoic acid or light ends fraction is removed as the top fraction of the first tower and PAN product fraction is removed as the top fraction of the second tower. Operating at such pressures, the impurities, mainly benzoic and o-toluic acids, can be readily removed at reflux ratios of from 10:1.0 up to 50:1.0 as a first or light ends fraction amounting to about one percent by weight more than the sum of the impurities content. For example, when the phthalide-free impure PAN has a total impurity content of 2.6 weight percent, the first fraction taken will amount to 3.6 weight percent of the impure PAN charged. Th reflux ratio will depend on the size of the light ends (benzoic acid-containing) impurity fraction relative to the feed. Minimum reflux ratio requirements are fixed by vapor-liquid equilibrium compositions and acceptable losses of PAN. As the reflux ratio is decreased, as evident to those skilled in the art, the PAN loss to the light ends fraction will increase.

The PAN product fraction can then be taken at a reflux ratio of from 1:1 to 5:1, preferably 1:1 to 2.5:1. There is left a residue (bottoms fraction of the second tower) containing a alkali metal hydroxide reaction products and condensation products whose formation (e.g., product of the reaction of phthalide with PAN and/or benzoic or o-toluic acid) is catalyzed by the hydroxide. Such bottoms or residue fraction will amount to about from 1 up to 5 weight percent of the PAN charged and will contain 25 to 50% PAN so that the residue as a liquid has a viscosity such that it does not present a fluid transfer (gravity flow or forced flow) problem. The use of a viscosity lowering addition agent can decrease said loss of PAN to the bottoms fraction.

The example to follow is provided to enable those skilled in the art to understand and practice the present invention.

EXAMPLE 1

Step (a). Continuous One-Step Oxidation

The oxidation reaction vessel used in this step of continuous neat oxidations of liquid o-xylene with air is of the stirred tank type and has an internal diameter of 15 cm, a height of 76 cm, and a total internal volume of 14 liters. The vessel is constructed of 9.5 mm thick titanium. The reaction vessel has an internal coil which can be used to either supply heat to the stirred liquid contents or to remove heat therefrom by indirect heat exchange between a fluid pumped through said coil and the stirred liquid reaction mixture. The vessel has valved inlets for introducing o-xylene, catalyst solution and one other liquid through flow meters into the upper portion of the vessel, a valved gas inlet for introducing compressed air into the bottom of the stirred reaction mixture, a heat-treated valved outlet in the lower portion of the stirred reaction mixture for its withdrawal from the vessel, and a gas outlet in the upper portion of the vessel for withdrawal of exhaust comprising spent air, carbon oxides, water vapor and xylene vapor from the oxidation vessel.

As auxiliary apparatus for the oxidation, there are interconnected a first vertical upflow condenser and a second vertical upflow condenser for series flow therethrough of exhaust gas transferred from its outlet in the oxidation vessel to the bottom inlet of the first vertical condenser. Said first vertical upflow condenser has a mean heat exchange area of 0.67 m$^2$ and said second vertical condenser has a mean heat exchange area of 0.39 m$^2$. An adjustable pressure control valve is in the gas exit line from the second vertical condenser and said valve is set to control the pressure in the oxidation vessel and the above condensation system. The two condensers each have their own cooling system of cool water or steam which can be supplied at a gauge pressure of from 0 up to 9/kg. cm$^2$. The decompressed exhaust gas substantially free of water and xylene is cooled to remove any remaining water and xylene and then flows to a wet gas test meter with a flow measuring capacity of 13,590 normal liters per hour. Following said meter there are gas sampling lines leading to CO$_2$, CO and O$_2$ analyzers prior to venting the exhaust to the atmosphere.

Thermowells are provided for measurement of temperature of the stirred reaction mixture, and the gas vented from each of the first and second vertical upflow condensers. The temperature of liquid reflux flowing back to the reaction vessel from the condensers is also measured.

In this oxidation of liquid o-xylene, benzoic acid miscibility aid is dissolved in the o-xylene feed and the system of catalysis is fed as an aqueous solution of the components.

The water solution of components of catalysis is prepared by dissolving in each 1.0 liter of water 230.4 grams of cobaltous acetate tetrahydrate, 486 grams of manganous acetate tetrahydrate and 107.2 grams of hydrobromic acid containing 48 weight percent hydrogen bromide. Such solution amounts to 1.52 liters per 1.0 liter of water used and contains the following weight percent of the indicated component.

TABLE III

| Component | Weight percent |
|---|---|
| Cobalt, as element | 2.98 |
| Manganese, as element | 5.96 |
| Bromine, as element | 2.98 |
| Water | 69.3 |

Such solution is fed at the rate of 8.64 milliliters per gram mole of o-xylene and furnishes 5.39 milligram atoms of cobalt, 11.6 milligram atoms of manganese and 3.98 milligram atoms of bromine per gram mole of o-xylene.

The oxidation is conducted at a reaction temperature varying from 216° to 227° C., at a gauge pressure of 24.6 kg/cm$^2$, with xylene fed at the rate of 8.57 gram moles/hr containing benzoic acid in an amount of 10.6 grams per 1.0 gram mole of xylene dissolved at 65° C. and the xylene solution fed at said 65° C. temperature, and with an air rate of 604 n liters of air per 1.0 gram mole of xylene. The exhaust gas from the oxidation vented from the second condenser is at the temperature of 102° C. and contains 12 vol.% O$_2$ on a benzoic acid and water-free basis. The xylene-water condensate had a volume ratio of xylene to water of 0.5 to 1.0. The residence time in the oxidation zone is 90 minutes.

The liquid effluent at 1.703 kg/hr from the oxidation zone by analysis is found to contain on a weight basis 73.5% o-phthalic acid, 11.2% benzoic acid, 0.19% o-toluic acid, 0.13% 2-carboxybenzaldehyde, 0.19% phthalide, 0.83% higher boiling compounds, and 13.95% water. Said flow of such liquid oxidation effluent represents an 88 mole percent (% of theoretical) yield of o-phthalic acid.

For the o-phthalic acid dehydration to PAN and its flash evaporation in step (b) of this example, the dehydration-evaporation vessel used is a thin film dehydration-evaporator having an evaporation surface of 2546 cm$^2$. Said evaporation surface is the surface of a horizontal cylinder rotatable in a tapered jacketed chamber. Said cylinder has on its surface four blades which have a 1.0 mm clearance from the inner jacket surface. The cylinder rotates at 1800 rpm for a tip speed of 10 m/sec. The vapor-liquid disengagement section is heated electrically to 180° C. The jacket is heated with circulating oil preheated to a temperature of 220° C. The jacket is co-extensive with the rotatable cylinder. A flanged glass residue receiver is located in the bottom of the vapor-liquid disengagement zone. A removable tubular vapor outlet containing a glass wool demister pad is connected to the feed inlet of a fractionation unit in which the reflux liquid is methylbenzoate.

An adjustable ram valve feeder is in the dehydrator-evaporator end of the fluid transfer line between the oxidation vessel wherein the catalytic neat oxidation of liquid o-xylene with air occurs at a gauge pressure of 24.6 kg/cm².

Step (b) Dehydration-Evaporation

The feed for the thin film evaporator comprises liquid oxidation effluent cooled to 200° C. and at a gauge pressure of 10.2 kg/cm². Said feed is introduced at a rate of 28.4 grams per minute into the thin film evaporation operated at a subatmospheric pressure of 210 to 230 mm Hg (0.276 to 0.30 atmosphere), at a feed section temperature of 230° C. and a liquid-vapor disengagement section temperature of 210° C. The residual liquid cooled from the evaporator amounts to about 2.2 weight percent of the oxidation effluent fed to the evaporator. Said residue contains on a weight basis 50% PAN, 10.4% benzoic acid, 0.4% o-toluic acid, 0.19% 2-carboxybenzaldehyde, 0.38% phthalide, and 38.5% higher boiling compounds including metal salts (from the metal catalyst components) of organic acids. The feed and vapor mixture compositions are, on a weight basis, shown in TABLE IV to follow.

TABLE IV

| Composition of Feed to and Vapor From Evaporator | | |
|---|---|---|
| Component, wt.% | Feed | Vapor |
| o-Phthalic Acid (Phthalic Anhydride | 93.5 | 65.2 |
| o-Toluic Acid | 0.19 | 0.18 |
| 2-Carboxybenzaldehyde | 0.13 | 0.13 |
| Phthalide | 0.19 | 0.18 |
| Benzoic Acid | 11.2 | 11.1 |
| High Boiling Compounds* | 0.83 | |
| Water | 13.95 | 22.1 |

*"High Boiling Compounds" include metal salts of organic acids.

The above vapor composition comprises 91.9% of the feed to the evaporator or 26.1 grams per minute of vapor mixture and can contain from 0.3 up to 0.8 weight percent organic bromides.

Step (c) Debromination

The 27.8 grams per minute of vapor mixture from step (a) at a temperature of 210° C. is passed through a bed of 125 grams of 1.69 up to 4.75 mm particles of palladium disposed on the surface of activated carbon having a palladium content of 0.5 weight percent and operated at a subatmospheric pressure of 0.22 atmosphere and a temperature of 210° C. Such catalyst loading is 1.0 kg/hr of vapor mixture for 74.9 grams of catalyst.

Step (d) Separation of Water Vapor From PAN

Said 26.1 grams/min of vapor mixture is fed to a fractionating column of the type before described but of larger volume for separation of water vapor from PAN by the use of methylbenzoate as reflux liquid. The volumetric reflux ratio of methylbenzoate to water is 20:1.0. The column is operated at a subatmospheric pressure of 150 mm Hg (0.197 atmosphere) and a reboiler temperature of 215° C. The liquid product drawn from the reboiler (21.57 grams per minute) contains on a weight basis 84.93% PAN, 0.24% o-toluic acid, 0.17% 2-carboxybenzaldehyde, 0.24% phthalide, and 14.4% benzoic acid.

Step (e) Removal of Phthalide

The liquid withdrawn from the foregoing step (d) is combined with 7.4 milligram moles of KOH per 1.0 gram mole of PAN and the mixture heated to a temperature of 275° C. at a residence time of four hours at 0.16 atmosphere while refluxing PAN. By such heating, the phthalide content of the liquid will be found by analysis to be less than 0.001 weight percent.

Step (f) Fractionation

The liquid from step (e) is charged to fractionation equipment operated at 0.13 atmosphere. A first (light ends) fraction is taken at a reflux ratio of 50:1 in an amount of 14.5 weight percent of the liquid charge as top fraction of the first tower. Said first fraction contains all the benzoic acid, o-toluic acid and 2-carboxybenzaldehyde but only a small amount (2%) of the PAN content of the materials charged to fractionation. The PAN product fraction is taken at a reflux ratio of 2.5:1 as top fraction from the second tower. Said product PAN fraction amounts to 97.5% of PAN content of the materials charged to fractionation. The bottoms fraction from the second tower, about one percent of the materials charged to the fractionation, contains about 50 weight percent PAN.

The product PAN fraction as a liquid will have an initial APHA color of 10 (Pt-Co scale) and an aged (ASTM Test Method D 1209-69) APHA Color of 40. The purity of the PAN product recovered from the foregoing process will be at least 99.8%.

The invention claimed is:

1. A process for preparing high purity phthalic anhydride which comprises the combination of the sequential continuous steps of (a) single-step neat oxidation of liquid o-xylene with air or air enriched to 50 volume percent oxygen with oxygen gas in a stirred oxidation zone operated at a temperature of from 200° C. up to 235° C. under a gauge pressure of from 23 up to 31 kg/cm² and for a residence time therein of from 90 up to 120 minutes, in the presence of from 2 up to 21 weight percent water and based on 1.0 gram mole of o-xylene in the presence of from 5 up to 20 grams of benzoic acid, from 0.5 up to 20 milligram atoms of cobalt, from 0.15 up to 20 milligram atoms of manganese and from 0.225 up to about 60 milligram atoms of bromine whereby a liquid mixture containing from 70 up of 85 weight percent o-phthalic acid is formed containing phthalide as one impurity; (b) rapid dehydration of o-phthalic acid content of said liquid mixture to phthalic anhydride at a pressure of from one atmosphere down to 0.05 atmosphere and a temperature of from 180° C. to 250° C. to rapidly vaporize said anhydride and water from the liquid mixture; (c) removal of bromine by contacting said vapor mixture with a noble metal catalyst; (d) separation of water vapor from said vaporized phthalic anhydride by direct contact in a fractionating system between the vapor mixture and a water immiscible and inert heat exchange liquid which boils at a temperature below the boiling temperature of said anhydride, is a liquid at a temperature below the freezing temperature of said anhydride, and is a solvent for said anhydride at a temperature between its freezing point and melting point wherefrom a water-free liquid impure phthalic anhydride at a temperature of from 200° C. up to 250° C. is removed as a bottom fraction from said fractionating system; (e) removal of phthalide from said liquid impure phthalic anhydride by heating it to a temperature of from 250° C. up to 350° C. in the presence of from 1.0 up to 10 milligram moles of potassium hydroxide; and (f) fractionation of said phthalide-free impure phthalic anhydride at a pressure of from 0.026 up to 1.0 atmosphere to remove a first fraction containing all of the benzoic acid, a second fraction comprising the phthalic anhydride product and a third fraction comprising materials boiling higher than phthalic anhydride.

2. The process of claim 1 wherein the heat exchange liquid in step (c) is methylbenzoate used in the liquid volume ratio of from 8:1 to 20:1 of methylbenzoate to water.

3. The process of claim 2 wherein the steps (b) through (e) are conducted at a pressure of from 0.13 up to 0.3 atmosphere.

4. The process of claim 3 wherein step (d) is conducted at 275° C. at a residence time of four hours.

* * * * *

UNITED STATES PATENT OFFICE
CERTIFICATE OF CORRECTION

Patent No. 4,215,054     Dated July 29, 1980

Inventor(s) Hobe Schroeder et al.

It is certified that error appears in the above-identified patent and that said Letters Patent are hereby corrected as shown below:

| Col. | Line | |
|---|---|---|
| 3 | 28 | "but the reactionxs" and should read --but the reaction's--. |
| 3 | 60 | "benzoic said" and should read --benzoic acid--. |
| 7 | 31 | "particle from" and should read --particle sizes from--. |

Signed and Sealed this

Twenty-fourth Day of August 1982

[SEAL]

Attest:

GERALD J. MOSSINGHOFF

*Attesting Officer*     *Commissioner of Patents and Trademarks*